(12) United States Patent
Busch

(10) Patent No.: US 8,486,378 B1
(45) Date of Patent: Jul. 16, 2013

(54) HUMAN FINGERNAIL STRENGTHENING AND CONDITIONING METHODS AND COMPOSITIONS UTILIZING NATURAL OILS

(76) Inventor: Francis W. Busch, Southbury, CT (US)

( * ) Notice: Subject to any disclaimer, the term of this patent is extended or adjusted under 35 U.S.C. 154(b) by 0 days.

(21) Appl. No.: 12/583,398

(22) Filed: Aug. 21, 2009

(51) Int. Cl.
*A61Q 3/00* (2006.01)
*A61K 8/97* (2006.01)
*A61Q 3/02* (2006.01)
*A61K 8/92* (2006.01)

(52) U.S. Cl.
CPC .. *A61Q 3/02* (2013.01); *A61K 8/922* (2013.01)
USPC ............................................. 424/61; 424/401

(58) Field of Classification Search
None
See application file for complete search history.

(56) References Cited

U.S. PATENT DOCUMENTS

| | | | | |
|---|---|---|---|---|
| 2,153,762 | A * | 4/1939 | Kritchevsky | 8/94.14 |
| 3,989,817 | A * | 11/1976 | Mayer | 424/61 |
| 4,286,609 | A * | 9/1981 | Miller | 132/75 |
| 4,407,884 | A * | 10/1983 | Witt | 428/220 |
| 5,403,402 | A * | 4/1995 | LeGrow | 134/38 |
| 5,578,297 | A * | 11/1996 | Mellul et al. | 424/70.7 |
| 5,968,986 | A * | 10/1999 | Dyer | 514/643 |
| 6,284,802 | B1 * | 9/2001 | Bissett et al. | 514/739 |
| 2004/0031500 | A1 * | 2/2004 | Reyzis | 132/200 |
| 2004/0234475 | A1 * | 11/2004 | Lannibois-Drean et al. | 424/70.12 |
| 2010/0158838 | A1 * | 6/2010 | Kergosien | 424/61 |
| 2010/0178262 | A1 * | 7/2010 | Kergosien et al. | 424/61 |

FOREIGN PATENT DOCUMENTS

JP  2004123638 A  *  4/2004

OTHER PUBLICATIONS

"Tea tree oil" Dorland's Illustrated Medical Dictionary, Elsevier (2007).*
"Fatty Acid Composition and Properties of Oils Chart", The Original Soap Dish (2002) accessed at http://thesoapdish.com/oil-properties-chart.htm, Feb. 26, 2012.*
21 CFR 178.3650, Code of Federal Regulations, Apr. 1, 2003 Ed., accessed at http://edocket.access.gpo.gov/cfr_2003/aprqtr/pdf/21cfr178.3690.pdf.*
Crews et al. (Journal of Agriculture and Food Chemistry, 53: 4853-4860 (2005).*
S.K. Oil Inc. "Raw linseed oil", accessed at http://skoil.in/raw-linseed-oil.html, Jul. 5, 2012.*
"MSDS Walnut Oil", accessed at http://www.naturalsourcing.com/msds/MSDS_Walnut_Oil.pdf, Jul. 5, 2011.*
"Resilient", accessed at http://thesaurus.com/browse/resilient?s=t, Jul. 5, 2012.*
"Harden", accessed at http://thesaurus.com/browse/hardening?s=t, Jul. 5, 2012.*

* cited by examiner

*Primary Examiner* — Kortney L Klinkel
*Assistant Examiner* — Lisbeth C Robinson

(57) ABSTRACT

A Natural oils composition for hardening and strengthening fingernails and toenails in which the natural oils contained therein exhibit ability to self polymerize into a solid film in the presence of oxygen. Oils of this invention are diluted with compatible solvents allowing penetration into the nail. Oils of this invention exhibit an Iodine Value greater than 140 grams of iodine absorbed per 100 grams of oil as measured under the prescribed conditions of a standard method described forthwith. Fingernail strengthening and conditioning compositions with antifungal properties are also disclosed.

9 Claims, No Drawings

HUMAN FINGERNAIL STRENGTHENING AND CONDITIONING METHODS AND COMPOSITIONS UTILIZING NATURAL OILS

BACKGROUND OF THE INVENTION

The field of the present invention is directed toward both a new composition and a new method using self polymerizing natural oils with an Iodine Value greater than 140 grams of iodine absorbed per 100 grams of oil under the prescribed conditions of the Hanus Method as fully detailed in the 2002 USP/NF published by The United States Pharmacopeia Convention, Inc. Rockville Md. 20852 Page 1935 and well known to those skilled in the art. The oils of this invention are diluted with compatible solvents which reduce the viscosity allowing penetration into nail.

Because of the difficulty growing beautiful long fingernails, commercial establishments have thrived providing customers with artificial fingernails that give the appearance dictated by this fashion objective. Unfortunately most artificial fingernails commercially available today exhibit a number of major problems. These problems include the time and expense required to install and the time and expense to maintain Beyond the issues of time and expense to install and maintain artificial fingernails, these products may cause severe damage to the underlying natural nail. Artificial fingernails are typically occlusive to water vapor and the natural nail onto which the artificial nail is glued becomes soft and saturated with moisture. This wet natural nail becomes susceptible fungal infection which is very difficult to cure. When the artificial nail is removed; the natural nail is often damaged during the removal process.

Treatments to strengthen natural nails in the prior art have frequently used formaldehyde which is a health hazard for many people and has been banned in many locations. Non formaldehyde prior art is disclosed in U.S. Pat. No. 5,478,551 issued to Francis W. Busch, Jr. (the current inventor) which teaches the use of fluoride compounds to harden and strengthen human fingernails. While the fluoride compositions of this art are effective, four weeks are required before the full benefit is realized. Additionally, there is a consumer preference for products that are effective and use natural ingredients rather than those of a synthetic nature.

The compositions and methods of the present invention are not subject to and overcome the disadvantages of known compositions and methods discussed above.

Natural oils have been used to moisturize and condition skin and fingernails for thousands of years. While said oils have been proven effective for moisturizing and conditioning fingernails and allow them to become more flexible, it is totally unexpected that application of oil to a fingernail could actually harden and strengthen the same fingernail. Even more unexpected is that the hardening and strengthening of the nail would occur within eight hours of application.

SUMMARY OF THE INVENTION

Accordingly, it is an object of the invention to provide new and improved compositions for hardening and strengthening fingernail and toe nails which employ natural oils that change from a liquid oil to a solid material after application to the fingernail or toe nail and thereby causing the desired effect. Oils of this invention are natural and polyunsaturated. They exhibit an Iodine Value greater than 140 grams of iodine absorbed per 100 grams of oil under the prescribed conditions of the Hanus Method as referenced above.

Another object of this invention to provide hardening and strengthening compositions for fingernails and toe nails where such effect is accomplished in as little as eight hours.

It is a further object of this invention to provide a new and improved method for hardening and strengthening fingernails and toe nails where diluting solvents allow the natural oils to penetrate into the treated nail prior to the conversion of the oil from a liquid to a solid.

These diluting solvents also allow the oils of this invention to quickly convert from a liquid to a solid coating.

It is a yet further object of this invention to provide compositions for hardening and strengthening fingernails and toe nails where said compositions are liquid and are conveniently applied to the nail.

An additional object of this invention is to provide compositions for hardening and strengthening fingernails and toe nails where resistance to bacterial and fungal infections results from inclusion of natural oils derived from the plant *melaluca alternifolia*.

These and other objects and advantages of this invention will either be explained are will become apparent hereinafter.

Preferred vegetable oils of this invention are:
Iodine Value
Flax seed Oil 175-204
Borage Oil 173-182
Black Currant Oil 173-183
Tung Oil 155-175
Oiticica Oil 179-218
Perilla Oil 195-208

The following fish oils are also suitable for fingernail strengthening of this invention:
Iodine Value
Cod liver oil 170
Menhaden oil 170
Sardine oil 185

The natural oil extracted from the plant *melaluca alternifolia* may be included to provide antifungal properties.

The natural oils of this invention are diluted with a compatible solvent that aids in the penetration of oils into the nail and shortens the drying time of the oils.

A compatible solvent is defined as one that when mixed with the oils of this invention in any ratio clear solutions result.

Particularly useful solvents of this invention are linear and branched aliphatic hydrocarbons such as hexane, heptane, isopentane, and the like and mixtures thereof.

A particularly useful solvent is Odorless Mineral Spirits Chemical Abstracts Number 64742-88-7 exhibiting a minimum flash point of 38 degrees centigrade where the flash point is measured using test method ASTM D7094-04. Test method ASTM D7094-04 is well known to those skilled in the art and is fully described in bulletin available from ASTM, Inc. located at 100 Barr Harbor Drive, West Cornshohocken Pa., United States of America.

Other solvents of this invention include Ethyl acetate, Butyl acetate.

Further useful solvents of this invention are blends of volatile silicones including the commercially available Methyl Siloxane Dow Fluid 345 available from the Dow Corning Corporation, Midland Mich. 48686. This commercially available blend combines Decamethylcyclopentasiloxane and Dodecamethylcyclohexasiloxane and is well know to those skilled in the art.

The solvent diluted natural oils of this invention are applied directly to the fingernail or toe nail. A particularly preferred natural oil of this invention is Perilla seed oil. Flax seed oil is also a particularly preferred oil of this invention. The Perilla Seed oil and Flax seed oil of this invention is commercially available from many sources including the Jedwards International Corporation of Quincy Mass., United States of America. Said oils are completely described in technical bulletins available from that company.

The ratio of solvent or blend of solvents to the natural oil or blends of natural oils may vary from 99 parts solvent and 1 part oil to 1 part solvent or solvent blend and 99 parts oil or oil blend.

The Example A as follows is a preferred example of this invention

EXAMPLE A

Formula in Parts by Weight
Odorless mineral Spirits 50 Parts
Perilla Seed Oil 40 Parts
Flax Seed Oil 9.5 Parts
Tea Tree Oil 0.50 Parts
Total: 100 Parts Experiment 1

The formula of Example A is applied to the clean unpolished fingernails often test subjects with a small brush and gently finger massaged into the nail and allowed to dry. Prior to the application the strength of each nail is measured as follows: A platform is used which positions the nail over a flattened cylinder. The cylinder creates a gap resulting from the curve of the nail positioned over the flat surface. Since the curve of the nail remains constant the distance from the nail to the top of the flattened cylinder remains constant. The force required to bend the nail flat against the cylinder is measured with WAGNER force gauge. The gauge measures the force to bend the nail in grams per square inch and is well known to those skilled in the art. Wagner force gauges are commercially available from Wagner Instruments, Inc., Greenwich, Conn., USA.

Results: Average 10 Subjects
FORCE TO BEND UNTREATED NAIL: 293 grams force per square inch.
FORCE TO BEND TREATED NAIL 8 hours post treatment: 540 grams force per square inch.

Example B is further particularly preferred formula of the present invention.

EXAMPLE B

Formula in Parts by Weight
Odorless Mineral Spirits 10.0 Parts
Perilla Seed Oil 44.7 Parts
Flax Seed Oil 44.8 Parts
Tea Tree Oil 0.50 Parts
Total 100 Parts Experiment B The formula of Example B is applied to the clean unpolished fingernails of ten test subjects with a small brush and gently finger massaged into the nail and allowed to dry. The strength of the nail was then measured as in Experiment A above.

Results: Average 10 subjects
FORCE TO BEND UNTREATED NAIL Example B: 340 grams force per square inch.
FORCE TO BEND TREATED NAIL EIGHT HOURS post treatment: 610 grams force per square inch.

The formula of Example B was further tested by 50 female subjects chosen based on their positive interest in their fingernail health and appearance.

Subjects applied the product once when receiving the sample (prior to 12 PM) and prior to retiring the same day. The product was applied three times a week for the remaining study period at their convenience approximately every other day. Subjects evaluated their nails prior to first application, eight hours after the second application, after one week and after four weeks. While no subject rated their nails as strong and resilient prior to first application, 43 of the subjects rated their nails as strong and resilient 8 hours after the second application.

The present invention has been described with respect to the preferred embodiments. Variations of the methods and compositions may be made without departing from the claims of the present invention. The protection sought is to be limited only by the terms of the claims which follow.

What is claimed is:

1. A method for hardening and strengthening fingernails or toe nails of human beings, the method comprising:
    applying a formula topically to an outer surface of fingernails or toe nails, the formula consisting of:
    Perilla Oil with an Iodine Value greater than 140 grams of iodine absorbed per 100 grams of oil present in an amount sufficient to provide hardening and strengthening of the nails upon penetration into the nails and optionally at least one additional natural oil; and
    a solvent for the natural oil and effective to cause the natural oil to penetrate into the fingernails or toe nails prior to conversion of the natural oil from a liquid to a solid; and
    allowing the formula to dry on the surface.

2. The method of claim 1 wherein the solvent is present in the formula in an amount in the range of 1 part solvent to 99 parts natural oil by weight, and 99 parts solvent to 1 part natural oil by weight.

3. The method of claim 1 wherein the solvent is a blend of Decamethylcyclopentasiloxane and Dodecamethylcyclohexasiloxane.

4. The method of claim 1 wherein the formula has at least one additional natural oil selected from Flax seed Oil, Borage Oil, Black Currant Oil, Tung Oil, and Oiticica Oil.

5. The method of claim 1 wherein the formula has at least one additional natural oil selected from Cod liver oil, Menhaden oil and Sardine oil.

6. The method of claim 1 wherein the formula has at least one additional natural oil from the plant *Melaleuca alternifolia* in an amount from 0.05 to 5.0 parts by weight.

7. The method of claim 1 wherein the solvent is an odorless mineral spirit.

8. The method of claim 1 wherein the step of applying the formula further comprises massaging the formula into the fingernails or toe nails prior to solidification.

9. The method of claim 1 wherein the formula is clear.

* * * * *